United States Patent [19]

Carroll et al.

[11] Patent Number: 5,361,640
[45] Date of Patent: Nov. 8, 1994

[54] MATERIALS TESTING APPARATUS FOR REDUCED SAMPLE BENDING

[76] Inventors: Norman L. Carroll, 156 Merritt Dr., Butler, Pa. 16001; Willard L. Pearce, 2315 Big Rock, Allison Park, Pa. 15101

[21] Appl. No.: 114,455

[22] Filed: Sep. 1, 1993

[51] Int. Cl.$^5$ .......................... G01N 3/08; G01N 3/20
[52] U.S. Cl. ...................... 73/831; 73/853; 73/856; 33/790
[58] Field of Search ............... 73/760, 788, 831, 849, 73/853, 826, 856; 33/501, 784, 787, 790, 712

[56] References Cited

U.S. PATENT DOCUMENTS

| | | |
|---|---|---|
| 2,454,850 | 11/1948 | Winkle et al. |
| 3,005,336 | 10/1961 | Wyman . |
| 3,107,524 | 10/1963 | O'Connor . |
| 4,686,860 | 8/1987 | Liu ........................ 73/856 |
| 4,845,997 | 7/1989 | Radin et al. .............. 73/856 X |
| 4,914,543 | 4/1990 | Carroll et al. ............ 361/294 |
| 5,138,887 | 8/1992 | Pohl ...................... 73/856 |
| 5,279,166 | 1/1994 | Ward et al. .............. 73/856 X |

FOREIGN PATENT DOCUMENTS

| | | | |
|---|---|---|---|
| 2534683 | 4/1984 | France | 33/790 |
| 3731460 | 4/1988 | Germany . | |

OTHER PUBLICATIONS

"Series 4100 Metals Testing Extensometers" pp. 4–6 dated by Aug. 1993 & 2 pages dated Jan. 1991 by Applied Test Systems Inc.

P. 15 "Coupling" (Refer to Bulletin 4030, presumably of Applied Test Systems, Inc.) published by Aug. 1993.

*Primary Examiner*—Thomas P. Noland

[57] ABSTRACT

A material testing apparatus is shown that uses one free swiveling alignment coupling and one alignment coupling which can be used in a free swiveling mode or a fixed alignment mode. These couplings and an alignment extensiometer are used to reduce sample bending. First and second pull rods (4,8) removably connected to the alignment couplings (5,9) are at opposite ends thereof removably coupled to the sample (1) being tested via sample couplings (3,7).

4 Claims, 3 Drawing Sheets

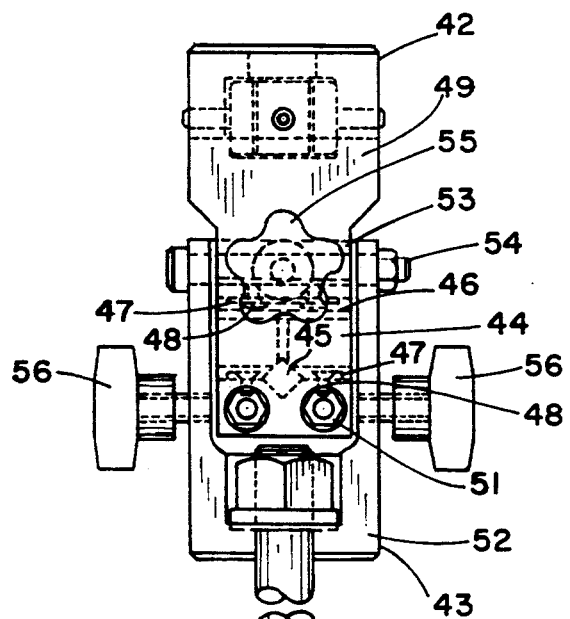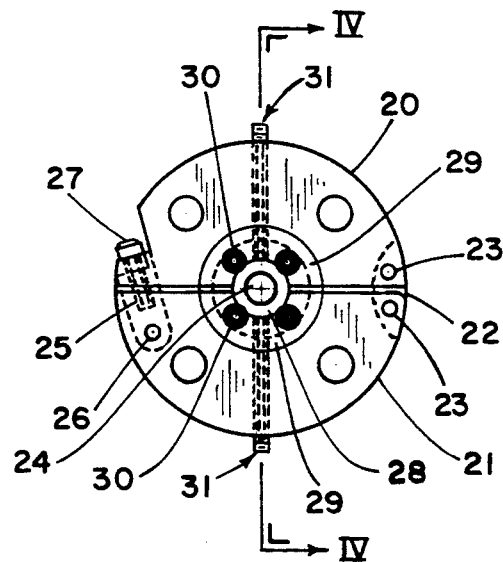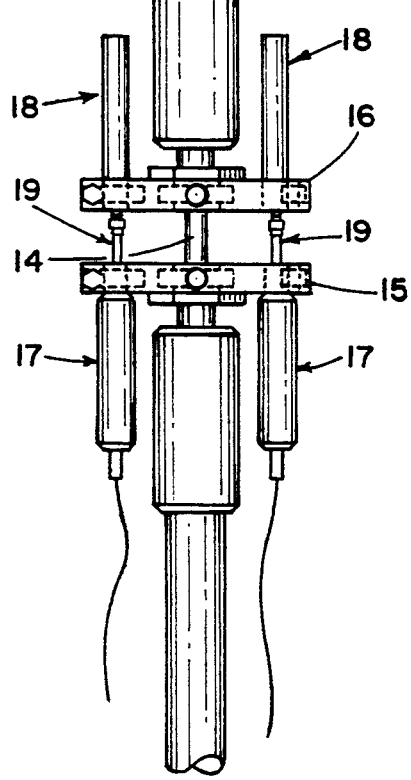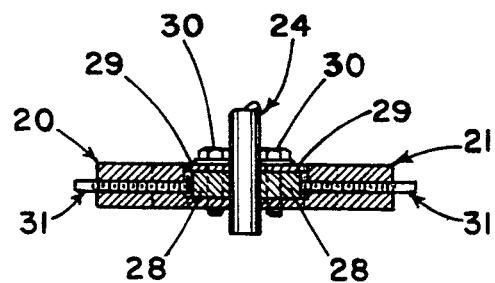
FIG.2
FIG.3
FIG.4

MATERIALS TESTING APPARATUS FOR REDUCED SAMPLE BENDING

BACKGROUND OF THE INVENTION

Materials testing apparatus is useful to measure the stress strain and yield strength of materials under carefully controlled conditions. When compression or tensile strength testing is done it is generally desireable to minimize the bending strains in the sample.

In tensile testing, the sample is generally placed between two pull rods while one rod remains fixed and the other experiences a load. Bending strains arise at the start of the test when the pull rods are not in perfect coaxial alignment or the sample is not in coaxial alignment with the pull rods.

The load is generally applied by use of a lever. The lever separates the pull rods thus stretching the sample, but, at the same time the sample stretches, the lever action moves the pull rods out of their original alignment. In this way dynamic bending strains arise in the sample.

Prior inventions have reduced the initial bending strain by interposing an alignment fixture between the load and the moving pull rod in the load train. The bending strain is measured on a dummy sample with an alignment extensiometer and the alignment fixture is used to align the pull rods in a fixed position so that the strains measured by an alignment extensiometer are equal on all sides of the dummy sample. The extensiometer is then removed and the dummy sample replaced with the test sample.

Prior inventions have also reduced some of the initial bending strain and some of the dynamic strain by interposing a free moving swivel, (lower alignment coupling), between the stationary pull rod and the fixed base and a second free moving swivel (upper alignment coupling) between the moving pull rod and the load train. As the load is applied or increased the couplings freely move so as to relax the bending of the sample until an equilibrium is established between the bending of the sample and the swiveling of the coupling.

Alignment fixtures and free moving alignment couplings do not eliminate bending strains. The present invention serves to reduce the bending strain and, if desired, to subject to the sample to a known bending strain.

SUMMARY OF THE PRESENT INVENTION

A novel coupling and extensiometer are used in the present invention to actively force the pull rods into a new alignment so as to reduce the bending strain experienced by a test sample. A knife edge coupling is designed to permit both free swiveling action and fixed alignment of the pull rods. The pull rods are pivotally mounted to the load and the base with double knife edge alignment couplings. One of the knife edge couplings is a free moving swivel. The second knife edge coupling is modified by introduction of four set screws which permit free swiveling motion when they are loosed to, change the angular alignment of the coupling as the screws are tightened and fix the angular alignment of the coupling when all are tightened.

An alignment extensiometer is specially designed to permit its use on the test sample. According to the preferred embodiment of the present invention, the alignment extensiometer consists of two cross heads removably attached by double compression fittings to the sample above and below the gage length. In this preferred embodiment of the invention a split insert is pressed against the sample by closure of the hinged cross head. Four separate linear displacement transducers are equally spaced around the test sample and removably fixed to one of the cross heads so as to measure the distance between the two cross heads. Together the transducers measure the bending strain in the sample.

The sample bending is reduced by using the four displacement transducers together with the four set screws. At first the four set screws are loosened and a partial load is applied to the sample. The knife edge couplings then freely swivel until the bending strain is partially removed. The transducers are zeroed for displacement then the load is increased. The four set screws in the specially designed knife edge coupling are then tightened one at a time to realign its pull rod. The tightening of the screws will cause the strain measured by the transducers to change and it is possible to tighten the screws in such a way so that the strain measured on all four transducers is equal. Once the measured strains are equal any loose set screws are tightened so that the alignment of the pull rods remains fixed in this desired alignment.

The four set screws can be electro-mechanically coupled to the transducers so the desired alignment is done automatically and an electro-mechanically coupled system can continuously adjust the set screws to equalize the strain measured in the four transducers during the course of a test, however, surprisingly, an electro-mechanical coupling is not necessary for many applications, and, the above combination of a free moving alignment coupling with a free moving coupling that may be fixed in position is sufficient to permit testing with minimal sample bending.

Although the use of four transducers with removable compression fit cross heads, four set screws in a modified knife edge coupling, and a conventional knife edge coupling is preferred it is possible to use this invention with a first alignment coupling having free swiveling motion, a second alignment coupling having means for free swiveling motion, means for adjusting the alignment and means for fixed alignment of the coupling, and an alignment checking fixture which is removably attached by a compression fitting means.

The present invention eliminates the need for dummy samples and assures alignment without disturbance of the load train. It allows for alignment compensation directly on the specimen and final alignment with less than 4% bending or final alignment with pre-set bending. The design allows for quick change of samples and stress testing in many applications without the need to realignment of the load train while the test is in process. It is a rugged design that can withstand the impulse of sample fracture and can be adapted to high temperature testing and various sample gauges and shapes. The present invention also permits the controlled misalignment of the pull rods when it is desired to test samples under bending strain conditions.

GENERAL DESCRIPTION OF THE DRAWINGS

FIG. 2 is an orthogonal front view of the sample, alignment extensiometer and modified knife edge alignment coupling.

FIG. 3 is an end view of the cross head.

FIG. 4 is a cut away side view of FIG. 3 with hinge and hinge pin not shown.

DETAILED DESCRIPTION OF THE INVENTION

Figure 1:
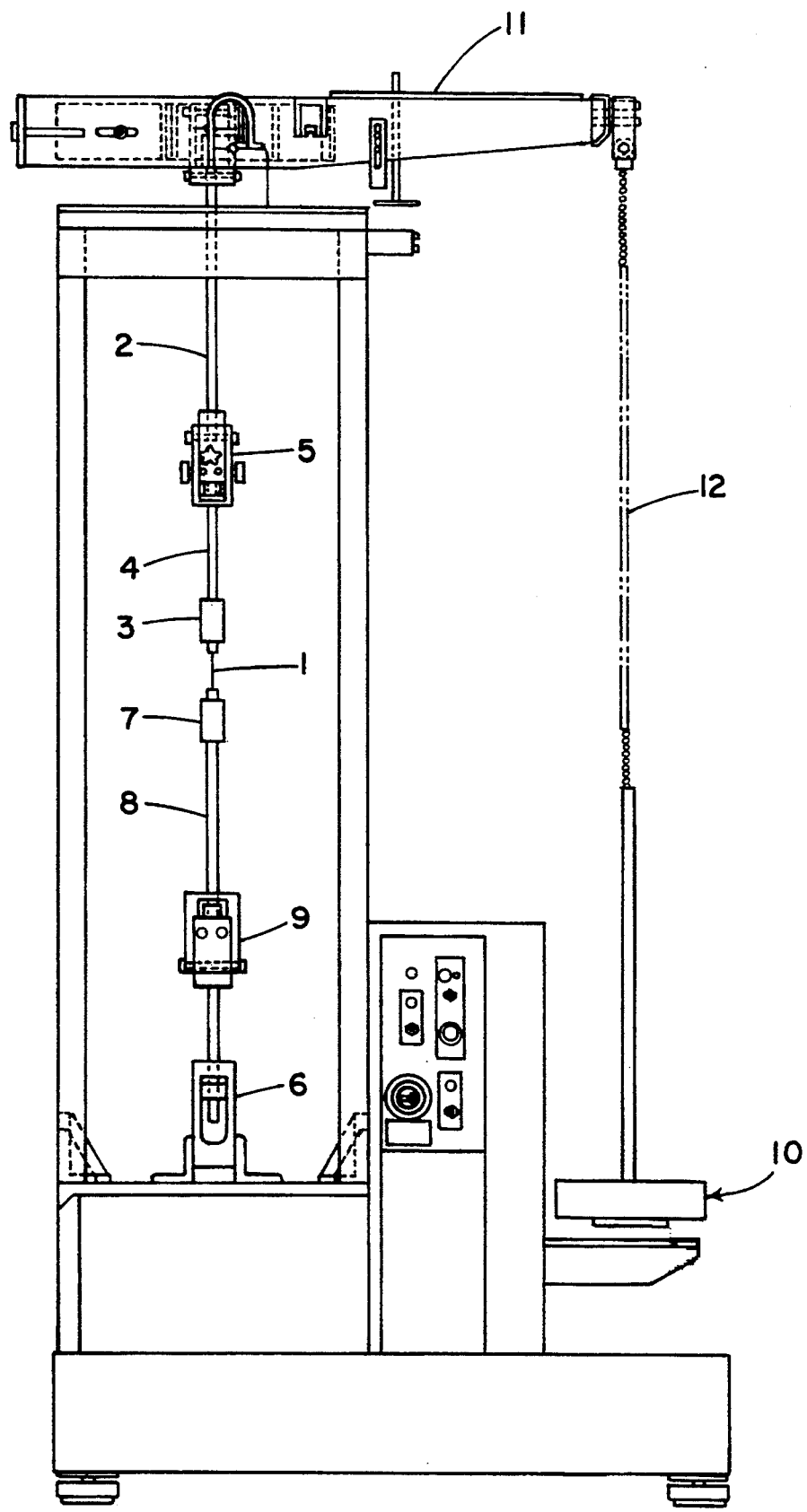
FIG. 1 is a lever arm testing apparatus, sample, and alignment couplings.

The present invention can be used with many different types of testing apparatus. For purposes of illustration, FIG. 1 shows a lever arm testing apparatus. The sample, 1, is joined to the load train 2 by an upper sample coupling 3, upper pull rod, 4, and modified knife edge coupling 5. The specimen, 1, is also joined to the base 6, through a lower sample coupling, 7, lower pull rod, 8, and lower knife edge alignment coupling, 9. The load 10, is applied to the load train 2, by way of a lever arm 11 and weight train 12.

FIG. 2 shows an alignment extensiometer in its position removably attached to the sample, 14. The alignment extensiometer consists of a lower cross head, 15, an upper cross head 16, and four variable capacitance transducers, 17. The preferred transducers are found in U.S. Pat. No. 4,914,543. The four transducers, 17, are removably attached to the lower cross head, 15, and four gage cylinders 18 are removably attached to the upper cross head, 16. It is preferred that the diameter of the gage cylinders, 18, be the same as the diameter of the transducers so that the upper and lower cross head, 15 and 16 are interchangeable. The checking fixtures 15 and 16 are attached to the sample so that each shaft, 19, rests on the opposing gauge cylinder, 18. This design permits the gauge cylinders, 18, to be advanced through the upper cross head to accommodate any limitation in the travel of the shaft.

FIGS. 3 and 4 show the cross head which is split in two parts, 20 and 21 and hinged, by a pivot arm, 22, and two dowel pins, 23, so that when the hinge is closed and locked in place with a pivot arm, 25, secured by a pivot pin, 26, and swivel nut, 27, the sample, 24, can be compressed against the two parts. Sample sizes and shapes vary, so the preferred design makes use of a split insert, 28, that is shaped to fill the space between the sample, 24, and the two parts of the cross head, 20 and 21. The split insert, 28, is fixed to the two parts, 20 and 21 by a compression plates, 29 and axial compression screws, 30. When the two parts are closed and locked in place about the sample the cross head becomes fixed to the sample by compression of the insert against the sample. If necessary, two radial compression screws 31 can be advanced thus pushing the split insert, 28 firmly against the sample 24 and the axial compression screws, 30 tightened.

Figure 5:
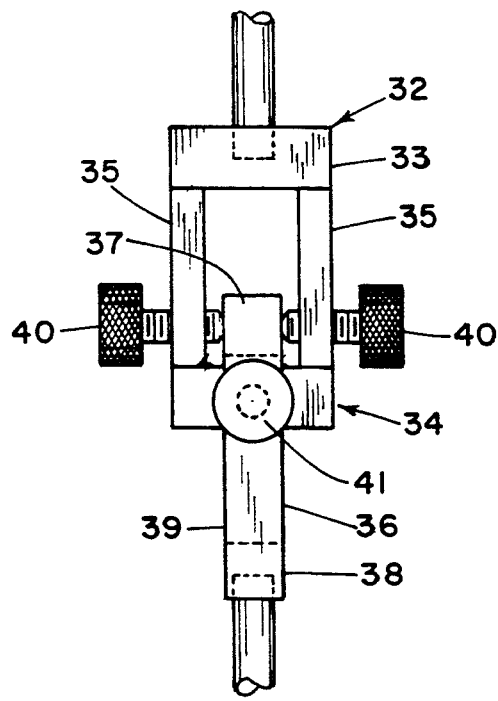
FIGS. 5 and 6 is an orthogonal view of a modified chain coupling.
Figure 6:
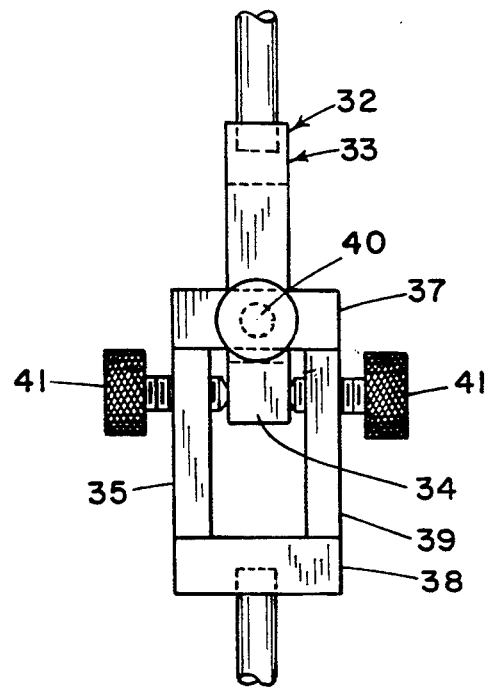

The alignment coupling is generally shown in FIGS. 5 and 6. It is chain like in construction comprising an upper link, 32, having a head, 33, a foot, 34 and two sides, 35 and a lower link, 36 having a head, 37 a foot, 38 and two sides, 39. Two set screws, 40 are threadedly engaged to the opposing sides of the upper link, 35. Each screw is adapted to engage the head of the lower link, 37. Two more set screws, 41 are threadedly engaged to the opposing sides of the lower link, 39. Again each screw is adapted to engage the foot of the upper link, 34.

Figure 7:
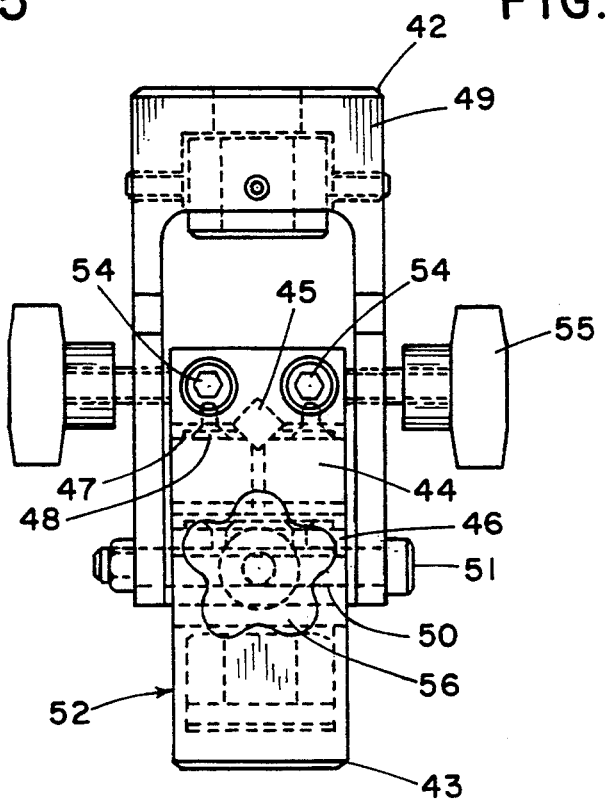
FIG. 7 is orthogonal side view of the modified double knife edge alignment coupling.

While the contact between the upper link and the lower link can be of many possible configurations, the preferred configuration is a double knife edge. FIGS. 2 and 7 show a front view and side view of the modified double knife edge alignment coupling. This is the preferred design for the chain coupling described above. The coupling is chainlike in construction with an upper link, 42 and a lower link, 43, separated by a floating v-block, 44 that is compressed between an upper knife edge, 45 and a lower knife edge, 46. The upper link consists of a buttonhead clevis, 49, closed with a shoulder block, 50, and secured with two shoulder bolts, 51. The lower link is a threaded clevis, 52, closed with a shoulder block 53 and secured with two shoulder bolts, 54. (The knife edges, 45 and 46, are secured to their shoulder blocks, 50 and 53, with brackets, 47 and screws, 48.) This double knife edge alignment fixture is modified to permit fixed alignment by the introduction of two pairs of knobbed set screws, 55 and 56. One pair of opposing set screws, 55 pass through the sides of the button head clevis, 49, and, when one is advanced, and the other withdrawn, the advancing screw applies pressure on a shoulder block, 53, and causes the threaded clevis, 52 to rotate on its knife edge, 46. Similarly, the second pair of opposing set screws, 56, pass through the sides of the threaded clevis, 52, and, when one is advanced, and the other withdrawn the advancing screw applies pressure on a shoulder block, 50 and causes the button head clevis, 49 to rotate on its knife edge, 45. The alignment coupling becomes fixed when both pairs of set screws are advanced and tightened against their shoulder blocks.

We claim:

1. In a materials testing apparatus wherein:
   a first pull rod is removably fixed to a sample and removably fixed to an alignment coupling,
   a second pull rod is removably fixed to the sample and removably fixed to a second alignment coupling,
   the improvement comprising:
   the first alignment coupling having means for free swiveling motion,
   the second alignment coupling having means for free swiveling motion, means for changing the alignment and means for fixing alignment,
   and an alignment checking fixture which is removably attached by a compression fitting means.

2. The materials testing apparatus in claim one wherein the alignment checking fixture comprising:
   an upper split and hinged disc with a centrally located split insert, removably fixed within the plane of the disc, and hinge means for pressing the portions of the split insert against the centrally located sample,
   a lower split and hinged disc with a centrally located split insert, removably fixed within the plane of the disc, and hinge means for pressing the portions of the split insert against the centrally located sample,
   and four linear displacement transducers with movable shafts equally spaced around the sample and removably fixed to the lower disc so that the shaft of each transducer engages the upper disc.

3. The materials testing apparatus of claim one wherein the means for free swiveling motion, changing the alignment and fixed alignment comprises a coupling of chain like construction comprising
   an upper link having a head a foot and two sides and
   a lower link having a head a foot and two sides and
   two set screws threadedly engaged to the opposing sides of the upper link, each screw adapted to engage the head of the lower link and two set screws threadedly engaged to the opposing sides of the lower link, each screw adapted to engage the foot of the upper link.

4. The materials testing apparatus of claim 3 wherein the upper link and lower link are separated by a floating v-block that is compressed between an upper knife edge and a lower knife edge.

* * * * *